United States Patent
Wagner

(10) Patent No.: US 11,040,147 B2
(45) Date of Patent: Jun. 22, 2021

(54) INJECTOR POSITION SENSING

(71) Applicant: ACIST Medical Systems, Inc., Eden Prairie, MN (US)

(72) Inventor: Reed B. Wagner, Bloomington, MN (US)

(73) Assignee: ACIST MEDICAL SYSTEMS, INC., Eden Prairie, MN (US)

(*) Notice: Subject to any disclaimer, the term of this patent is extended or adjusted under 35 U.S.C. 154(b) by 414 days.

(21) Appl. No.: 16/198,071

(22) Filed: Nov. 21, 2018

(65) Prior Publication Data

US 2019/0151560 A1 May 23, 2019

Related U.S. Application Data

(60) Provisional application No. 62/589,317, filed on Nov. 21, 2017.

(51) Int. Cl.
  *A61M 5/315* (2006.01)
  *A61M 5/145* (2006.01)
  *A61M 5/168* (2006.01)

(52) U.S. Cl.
  CPC .... *A61M 5/31568* (2013.01); *A61M 5/14566* (2013.01); *A61M 5/16831* (2013.01);
  (Continued)

(58) Field of Classification Search
  CPC ...... A61M 2205/3365; A61M 2205/52; A61M 5/14566; A61M 5/31541; A61M 5/31568;
  (Continued)

(56) References Cited

U.S. PATENT DOCUMENTS

| 1,165,686 A | 12/1915 | McElroy |
| 1,348,796 A | 8/1920 | Gronbech |

(Continued)

FOREIGN PATENT DOCUMENTS

| EP | 302248 A1 | 2/1989 |
| EP | 599649 A1 | 6/1994 |

(Continued)

OTHER PUBLICATIONS

ACIST CVi Contrast Delivery System User Manual, (P/N 900420-001 Rev. 4), Nov. 2005, 91 pages.

*Primary Examiner* — Jason E Flick
(74) *Attorney, Agent, or Firm* — Fredrikson & Byron, P.A.

(57) ABSTRACT

Injection systems can include a reservoir, a plunger mounted within the reservoir, and a plunger shaft including engaging the plunger within the reservoir. A motor can be coupled to the plunger shaft and can be configured to cause the plunger and plunger shaft to move within the reservoir. Systems can include a first encoder and a second encoder and a controller array in communication with the first and second encoders. The controller array can receive outputs from the first and second encoders representative of the position of the motor. Outputs from one encoder can be used to confirm the accuracy of the output of the other encoder. The controller can compare the outputs from the encoders, and, if the difference in the outputs is greater than a predetermined amount, disable operation of the motor.

20 Claims, 9 Drawing Sheets

(52) U.S. Cl.
CPC . *A61M 5/31541* (2013.01); *A61M 2205/3365* (2013.01); *A61M 2205/52* (2013.01)

(58) Field of Classification Search
CPC .......... A61M 5/16831; A61M 5/31565; A61M 5/31566; A61M 5/315; A61M 2205/33; A61M 2205/50; A61M 5/31533; A61M 5/31535; A61M 5/168
See application file for complete search history.

(56) References Cited

U.S. PATENT DOCUMENTS

| | | | |
|---|---|---|---|
| 3,147,753 | A | 9/1964 | Nogier et al. |
| 3,742,949 | A | 7/1973 | Hill |
| 3,890,956 | A | 6/1975 | Moorehead |
| 4,215,701 | A | 8/1980 | Raitto |
| 4,266,557 | A | 5/1981 | Merry |
| 4,869,720 | A | 9/1989 | Chernack |
| 4,952,208 | A | 8/1990 | Lix |
| 5,007,904 | A | 4/1991 | Densmore et al. |
| 5,085,638 | A | 2/1992 | Farbstein et al. |
| 5,181,912 | A | 1/1993 | Hammett |
| 5,299,559 | A | 4/1994 | Bruce |
| 5,314,416 | A | 5/1994 | Lewis et al. |
| 5,383,858 | A | 1/1995 | Reilly et al. |
| 5,411,489 | A | 5/1995 | Pagay et al. |
| 5,453,093 | A | 9/1995 | Haining |
| 5,620,423 | A | 4/1997 | Eykmann et al. |
| 5,735,825 | A | 4/1998 | Stevens et al. |
| 5,875,976 | A | 3/1999 | Nelson et al. |
| 5,947,929 | A | 9/1999 | Trull |
| 6,511,459 | B1 | 1/2003 | Fago |
| 6,752,789 | B2 | 6/2004 | Duchon et al. |
| 7,547,297 | B2 | 6/2009 | Brinkhues |
| 7,797,932 | B2 | 9/2010 | Herrick et al. |
| 8,118,781 | B2 | 2/2012 | Knopper et al. |
| 8,540,683 | B2 | 9/2013 | Williams, Jr. et al. |
| 8,613,730 | B2 | 12/2013 | Hieb et al. |
| 9,352,105 | B2 | 5/2016 | Hieb et al. |
| 9,381,300 | B2 * | 7/2016 | Smith ............... A61M 5/16877 |
| 9,925,338 | B2 | 3/2018 | Hieb et al. |
| 2002/0022807 | A1 | 2/2002 | Duchon et al. |
| 2004/0122369 | A1 | 6/2004 | Schriver et al. |
| 2006/0069356 | A1 | 3/2006 | Witowski |
| 2008/0183131 | A1 | 7/2008 | Duchon et al. |
| 2013/0096495 | A1 | 4/2013 | Holmqvist |
| 2013/0317436 | A1 * | 11/2013 | Ning ................ A61M 5/14566 604/152 |
| 2018/0304014 | A1 | 10/2018 | Knudsen |
| 2019/0328973 | A1 | 10/2019 | Cowe |

FOREIGN PATENT DOCUMENTS

| | | |
|---|---|---|
| JP | H07313598 A | 12/1995 |
| JP | 2001507963 A | 6/2001 |
| JP | 2001520087 A | 10/2001 |
| JP | 2005511158 A | 4/2005 |
| WO | 9201485 A1 | 2/1992 |
| WO | 9630066 A1 | 10/1996 |
| WO | 9920330 A1 | 4/1999 |
| WO | 9955401 A1 | 11/1999 |
| WO | 02096487 A1 | 12/2002 |
| WO | 2007062315 A2 | 5/2007 |
| WO | 2008134751 A1 | 11/2008 |
| WO | 2010062804 A1 | 6/2010 |
| WO | 2010062807 A1 | 6/2010 |

* cited by examiner

INJECTOR POSITION SENSING

PRIORITY CLAIM

This application claims priority to U.S. provisional patent application No. 62/589,317, filed Nov. 21, 2017.

TECHNICAL FIELD

The present disclosure pertains to injection systems and more particularly to apparatus and methods monitoring the position of one or more components thereof.

BACKGROUND

Fluid injection systems, which are used to inject a medical fluid into a patient, often include one or more sources, to hold the medical fluid, and one or more pressurizing units, to inject the medical fluid. For example, a contrast media powered injection system may include a source of contrast media coupled to a pressurizing unit, from which contrast is injected, to facilitate imaging during certain medical procedures, such as an angiographic or computed tomography (CT) procedure.

The pressurizing units of medical fluid injection systems typically include at least one reservoir and a plunger mounted therein. The plunger is moved, for example, by a motorized plunger shaft of the unit, in a first direction, to draw fluid into the reservoir, from the one or more sources, and then, in a second direction, to expel the fluid from the reservoir and into the patient, for example, via a catheter, which is coupled to the pressurizing unit. Pressurizing units of many medical fluid injections systems typically employ reservoir and plunger subassemblies that are disposable. These disposable reservoir and plunger subassemblies may be packaged as a set, wherein the plunger is mounted in the reservoir. Once assembled into the pressurizing unit, the reservoir and plunger may have an operational life spanning multiple injections, for example, preferably up to 10 or more injections. For those pressurizing units that include a permanent plunger shaft, or ram, assembling the reservoir and plunger therein includes coupling the shaft to the plunger prior to an injection; and, removing the reservoir and plunger from the pressurizing unit, after one or more injections (for example, for replacement with a new reservoir and plunger set), includes decoupling of the shaft from the plunger so that the reservoir and plunger may be separated from the shaft.

SUMMARY

Aspects of the instant disclosure relate to injection systems and methods of operating injection systems. Systems can include a plunger within a reservoir, a plunger shaft configured to engage the plunger, and a motor configured to move the plunger shaft longitudinally with respect to the reservoir. Systems can further include a first encoder and a second encoder that can be configured to output data representative of the position of the motor. In some examples, the first and second encoders comprise a multi-turn encoder and a sing-turn encoder, respectively.

Systems can include a controller array in communication with the first and second encoders. The controller array can be configured to determine a position of the plunger within the reservoir based on data received from one or both encoders. In some examples, the controller array is configured to compare the output of the first encoder and the second encoder. In some such examples, if the difference between the outputs is greater than a predetermined threshold, the controller array can disable operation of the motor.

In some examples, the controller array is configured to cause the motor to move the plunger shaft such that the plunger moves to a predetermined location within the reservoir based on feedback from the determined position of the plunger within the reservoir In some examples, a determined position of the plunger can be based on one of a single-turn encoder and a multi-turn encoder, and the other of the single-turn encoder and multi-turn encoder can be used to confirm the determined position of the plunger.

BRIEF DESCRIPTION OF DRAWINGS

The following drawings are illustrative of particular methods and embodiments of the present disclosure and, therefore, do not limit the scope of the invention. The drawings are not to scale (unless so stated) and are intended for use in conjunction with the explanations in the following detailed description. Methods and embodiments will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary methods and embodiments. Examples of constructions, materials and dimensions are provided for selected elements, and all other elements employ that which is known to those of skill in the field of the invention. Those skilled in the art will recognize that many of the examples provided have suitable alternatives that can be utilized.

Figure 1:
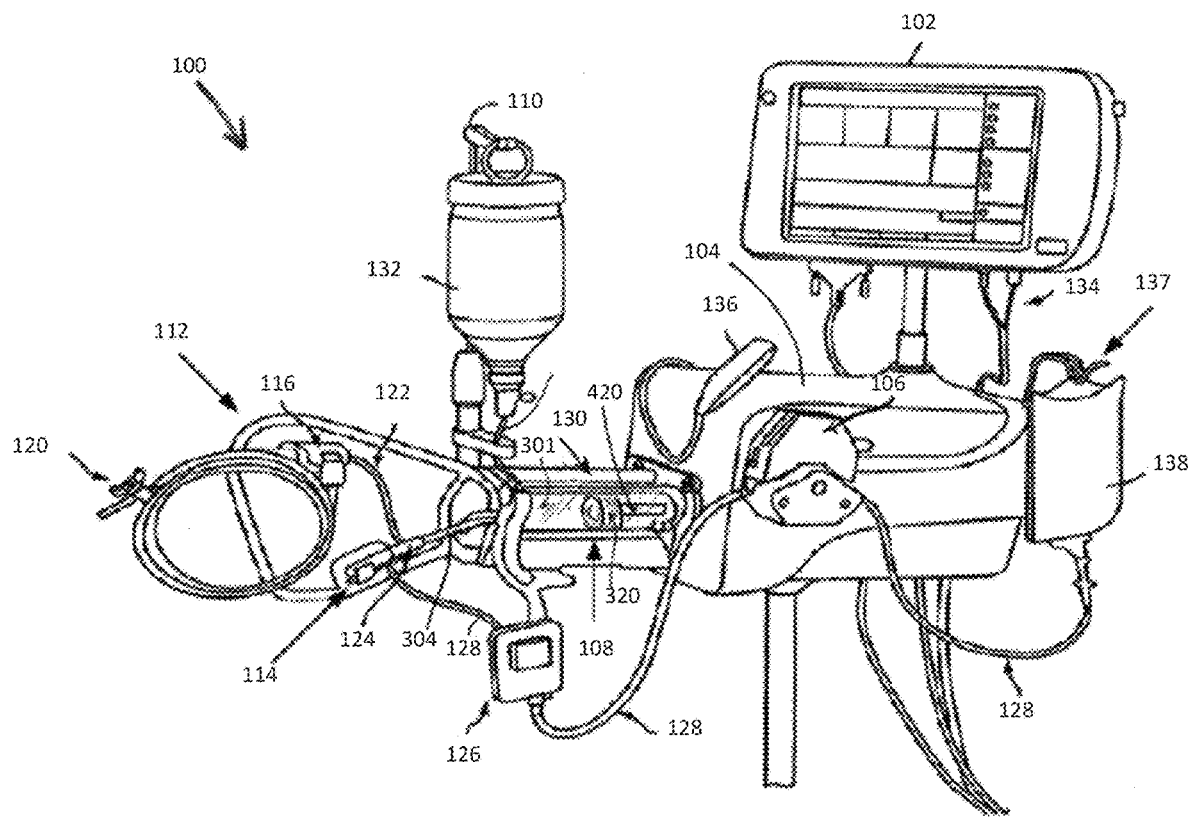
FIG. 1 is a perspective view of a fluid injection system, which may incorporate embodiments of the present invention.

FIG. 1 is a perspective view of a fluid injection system 100, which may incorporate embodiments of the present invention. FIG. 1 illustrates system 100 including, a fluid pressurizing unit 130 mounted in a sleeve 108 that extends from an injector head 104 of system 100, and a first fluid source 132. Source 132 is shown hanging from a holder 110 and being coupled to pressurizing unit 130, via an input tubing line 308, in order to supply fluid, for example, a contrast agent, to unit 130. Fluid pressurizing unit 130 is shown including a reservoir 301, in which a plunger shaft 420 extends, and a plunger 320, which is mounted in reservoir 301 and coupled to a plunger shaft 420.

According to the illustrated embodiment, shaft 420 is coupled to a motor assembly, which is contained in injector head 104 and which actuates shaft 420 to drive plunger 320 in reciprocating directions within reservoir 310. Injector head 104 may include a programmable controller array to drive the motor assembly. In some embodiment, the controller array includes a digital computer, which may be programmed, for example, via a control panel 102 of system 100. The controller array may further include a motor drive circuit, amplifier, tachometer, potentiometer, rectifier, pressure sensing load cell and ND converter, for example, as described in column 10, line 45-column 11, line 2 of commonly-assigned U.S. Pat. No. 6,752,789, which passage is hereby incorporated by reference. When shaft 420 is actuated to move plunger 320 proximally, toward injector head 104, in a suction stroke, fluid, from source 132, is drawn into reservoir 301, via input line 308, and, when shaft 420 moves plunger 320 distally, in a compression stroke, the fluid is expelled out from reservoir 301, through an output tubing line 304. FIG. 1 further illustrates output tubing line 304 coupled to a tubing line 122, which is mounted on a module 112 of system 100; tubing line 122 may be connected to a patient line, via a connector 120, so that the fluid, which is expelled from reservoir 301, is injected into a patient, for example, to facilitate imaging.

With further reference to FIG. 1, system 100 includes a second fluid source 138, which hangs from a hook 137 and from which fluid, for example, a diluent, such as saline, is drawn by a peristaltic pump 106, through a tubing line 128; pump 106 is shown mounted on injector head 104. System 100 further includes a manifold sensor 114 and a manifold valve 124, for controlling the flow of fluids into tubing line 122, either from tubing line 128, or from pressurizing unit 130, via tubing line 304. Manifold valve 124 may comprise a spring-biased spool valve, or another type of valve, for example, a check valve. Manifold sensor 114 can detect the position of manifold valve 124 and report this position to injector head 104.

A pressure transducer 126 is shown coupled to tubing 128. When tubing 122 is connected to a patient line that extends within a patient, pressure transducer 126 is capable of functioning as a hemodynamic monitor for the patient. Pressure transducer 126 converts detected pressures into electrical signals that may be monitored or otherwise used by system 100 or another monitoring device. An air bubble detector 116 is shown coupled to tubing line 122. Detector 116 is capable of generating an alarm signal, upon detection of a measurable, or otherwise significant, amount of air within tubing line 122. In addition, system 100 may automatically pause, or terminate, a fluid injection procedure, when detector 116 detects air in the tubing.

An operator of system 100, such as a clinician, may use control panel 102 of system 100 to set up various parameters and/or protocols to be used for a given injection procedure. The operator may interact with control panel 102, for example, via a touch-screen panel, to enter injection parameters for flow rate, maximum injection volume, maximum injection pressure, rise time, or other parameters. Control panel 102 may further display operating parameters of system 100 to the operator, and/or warning or alarm messages, for example, indicating that air has been detected by air bubble detector 116.

FIG. 1 also shows a hand-control device 136 coupled to control panel 102, via a connector 134, which may be connected to, or disconnected from, control panel 102. An operator may manipulate hand-control device 136 to control injection of fluid from system 100. For example, the operator may use hand-control device 136 as a variable-rate control device to variably control the rate of flow of fluid from system 100 (e.g., flow of fluid out of pressurizing unit 130). Hand-control device 136 may comprise an electrical device or a pneumatic device.

Because system 100 may deliver many injections over a number of patient procedures, injection fluids may need to be continuously replaced. Injector head 104 may automatically replenish fluid to reservoir 301, for example, based upon monitoring of injection volumes therefrom and comparing to an initial, input, volume; or the operator of system 100 may need to manually initiate a fluid replenishment procedure, upon detection that a fluid volume within reservoir 301 has been depleted to a critical volume. It should be noted that injector head 104 may automatically replenish fluid to reservoir 301 based upon operational state information, other than injection volumes. For example, if injector head 104 determines that system 100 is currently delivering fluid from pump 106, but not from reservoir 301, and that reservoir 301 is not filled to capacity, injector head 104 may cause the motor assembly to actuate plunger shaft 420 in order to draw additional fluid into reservoir 301, via input line 308.

Figure 2:
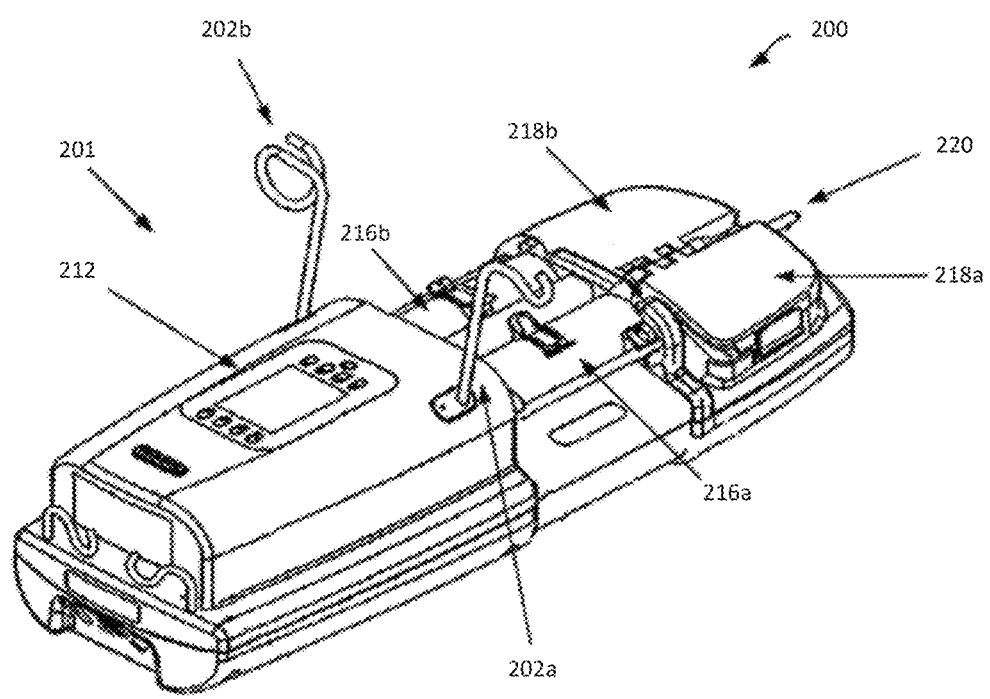
FIG. 2 is a perspective view of an alternative fluid injection system, which may also incorporate embodiments of the present invention.

Turning now to FIG. 2, an alternative fluid injection system 200 is shown in perspective view. Like system 100, system 200 may incorporate embodiments of the present invention. FIG. 2 illustrates system 200 including a control panel 212, which is mounted on an injector head 201 of system 200, and first and second sleeves 216A, 216B, which each extend between injector head 201 and a corresponding one of first and second front end assemblies 218A, 218B of system 200. FIG. 2 further illustrates system 200 including first and second source holders 202A, 202B, and, although not shown, it should be appreciated that a source mounted on each of holders 202A, 202B supplies a fluid to a corresponding fluid pressurizing unit, which is contained in the corresponding sleeve 216A, 216B.

Each fluid pressurizing unit of system 200 may be very similar to unit 130 of system 100 and include a reservoir, which is mounted in one of sleeves 216A, 216B, a plunger, which is mounted in the reservoir, and a plunger shaft, which extends from injector head 201, into the reservoir, and is coupled to the plunger. Furthermore, like system 100, a motor assembly may be coupled each of the plunger shafts, to actuate each shaft, independently, in order to drive the corresponding plunger in reciprocating directions, for alternating suction and compression strokes. The motor assemblies are contained within injector head 201 and may be controlled and monitored by one or more processors of a programmable controller array, also included in head 201. It should be understood that first and second front end assemblies 218A, 218B, of system 200, contain input and output tubing lines for each pressurizing unit, wherein each input tubing line supplies fluid from the corresponding source to the corresponding reservoir, and each output tubing line carries fluid expelled from the corresponding reservoir to a patient line, via a manifold valve. FIG. 2 illustrates a guide rod 220, which facilitates connection of the patient line to system 200. One of the pressurizing units of system 200 may expel a contrast agent for injection into the patient, via the connected patient line, and the other pressurizing unit, a diluent, such as saline. Valves and sensors, similar to those described above for system 100, may be incorporated into the tubing lines of system 200, which are contained within front end assemblies 218A, 218B, in order to facilitate the operation of system 200.

FIGS. 3A-3D show various operating conditions of an exemplary plunger/reservoir configuration. As shown in each of FIGS. 3A-3D, plunger 320 is positioned in reservoir 301. The reservoir 301 is in fluid communication with an input tubing line 308 and an output tubing line 304. Valves 68 and 64 can be used to selectively open and close fluid communication between the reservoir 301 and the input tubing line 308 and the output tubing line 304, respectively. While shown as being coupled to the reservoir 301 via separate ports, in some examples, the input and output tubing lines can both interface with the reservoir 301 via a single port. In some embodiments, one or both of valves 64 and 68 can be controlled via a controller array. A plunger shaft 420 can be configured to engage with plunger 320 in order to move the plunger 320 within the reservoir 310. In some embodiments, the plunger 320 may be configured to engage with the plunger shaft 420 such that distal or proximal motion of the plunger shaft 420 generally results in distal or proximal motion of the plunger 320 within the reservoir 310. Some such configurations are described in U.S. Pat. No. 9,352,105, which is assigned to the assignee of the instant application, and the relevant portions of which are hereby incorporated by reference in their entirety.

Figure 3A:
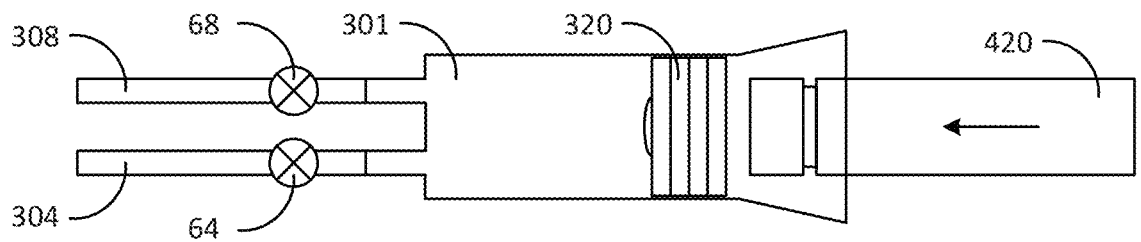
FIGS. 3A-3D show various operating conditions of an exemplary plunger/reservoir configuration.
Figure 3B:
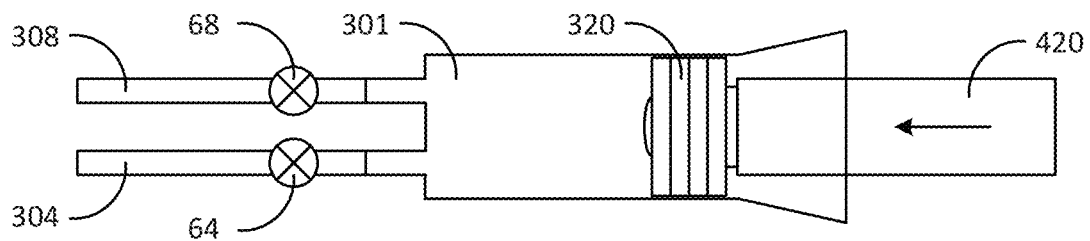
Figure 3C:
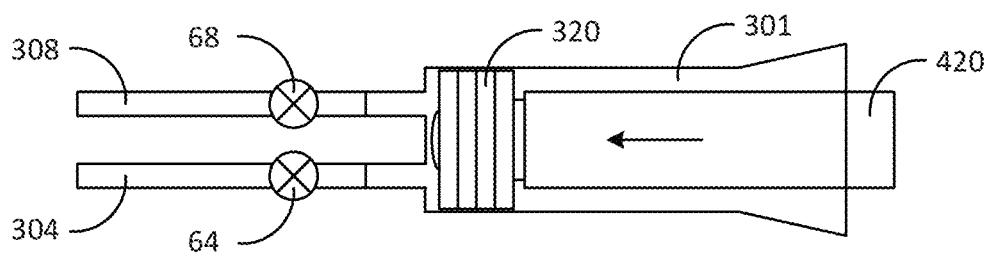

As will be understood by those having ordinary skill in the art, combined operating states of valves 64 and 68 as well as motion of the plunger 320 within the reservoir 301 (e.g., via the plunger shaft 420) can result in various injector operations. For example, in some embodiments, plunger shaft 420 can be moved distally as indicated via the arrow in FIG. 3A in order to engage plunger 320 within the reservoir 301. Once engaged, the plunger shaft 420 and plunger 320 can move together within the reservoir 301. In an exemplary embodiment, if a medium to be expelled from the injection assembly is present in reservoir, output line valve 64 can be opened and the plunger 320 can be moved distally via the plunger shaft 420 (e.g., as shown in FIGS. 3B and 3C).

Figure 3D:
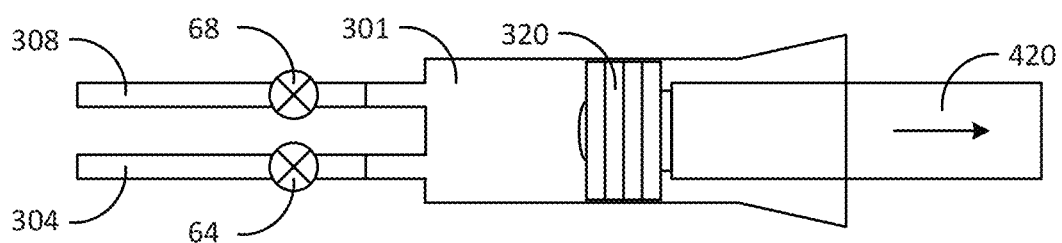

Pressure from the plunger 320 on the medium to be expelled forces the medium to be expelled from the output tubing line 304 via valve 64. In other operating examples, a plunger 320 at the distal end of reservoir 301 can be moved proximally via plunger shaft 420, such as via the arrow in FIG. 3D. In some such examples, a vacuum created within the reservoir 301 can be used to draw media into the reservoir via the input tubing line 308 (e.g., via valve 68) from a source (e.g., source 132 in FIG. 1). In other examples, maintaining both valves 64 and 68 in a closed position and extracting the plunger 320 as shown in FIG. 3D can result in disengagement of the plunger 320 from the plunger shaft 420 when the plunger 320 is extracted to or past a certain location, such as described in U.S. Pat. No. 9,352,105. These and other injection operations via activation of valves 64 and/or 68 and/or motion of the plunger 320 within the reservoir 301 will be understood by those having ordinary skill in the art.

As described, in various examples, plunger shaft 420 can be moved distally or proximally (e.g., to engage and/or disengage and/or move plunger 320 within reservoir) via a motor coupled to the plunger shaft. Such a motor can be controlled, for example, via a controller array and/or an external controller, such as control panel 102 or an external computer or workstation. In some embodiments, the controller array can be configured to drive the plunger shaft 420, and likewise, the plunger 320, by a predetermined amount and/or to a predetermined location. In various embodiments, such a controller array can be similarly configured to control one or more additional system components, such as valve 64 and/or valve 68, in order to execute one or more injection operations Exemplary systems can include one or more position sensors to provide feedback to the controller array regarding the position of the plunger 320, the motor, or the like. For example, a linear encoder or other sensor can be used to provide information regarding the position of the plunger 320 within the reservoir 301. Additionally or alternatively, one or more rotary encoders can be used in conjunction with the motor to determine the rotational position of the motor. In some such examples, the rotary position of the motor can be calibrated with the linear position of the plunger 320 within the reservoir 301 such that the position of the plunger can be determined using the rotary encoder data.

Position information regarding the position of the plunger 320 within the reservoir 301 (e.g., via a known position of the plunger, the motor, etc.) can be used to determine various parameters. For example, the position of the plunger 320 within the reservoir 301 can be indicative of an amount of injectable media present in the reservoir 301. Similarly, changes in the position of the plunger 320 within the reservoir 301 can be indicative of changes in the amount of injectable media present in the reservoir 301 (e.g., an amount added to or expelled from the reservoir 301). Such information can be useful to know when an operation should be performed (e.g., the reservoir 301 should be refilled from the source 132), when an operation is complete (e.g., a predetermined amount of media has been expelled), or the like. Accordingly, in some embodiments, such position information can be used to establish and/or perform certain system operations.

In some embodiments, when position information regarding the position of the plunger within the reservoir is used to control one or more aspects of operation of the system, uncertainty or error in the position information can lead to operating errors of the system. For example, in some cases, errors in the position information regarding the position of the plunger in the syringe can lead to an unknown amount of injectable media being present in the reservoir. In some such cases, system operations (e.g., injection of injectable media) may be performed incorrectly (e.g., attempting an injection with insufficient injectable media present in the reservoir, an incorrect amount of injectable media is injected, etc.). Such errors can lead to unsafe operation, and can cause damage to a patient and/or system equipment. Accordingly, in some embodiment, a system includes redundancy by determining the position of the plunger within the reservoir in multiple ways. If the position information from multiple measurements agree, it is less likely there is an error in the position information.

Figure 4:
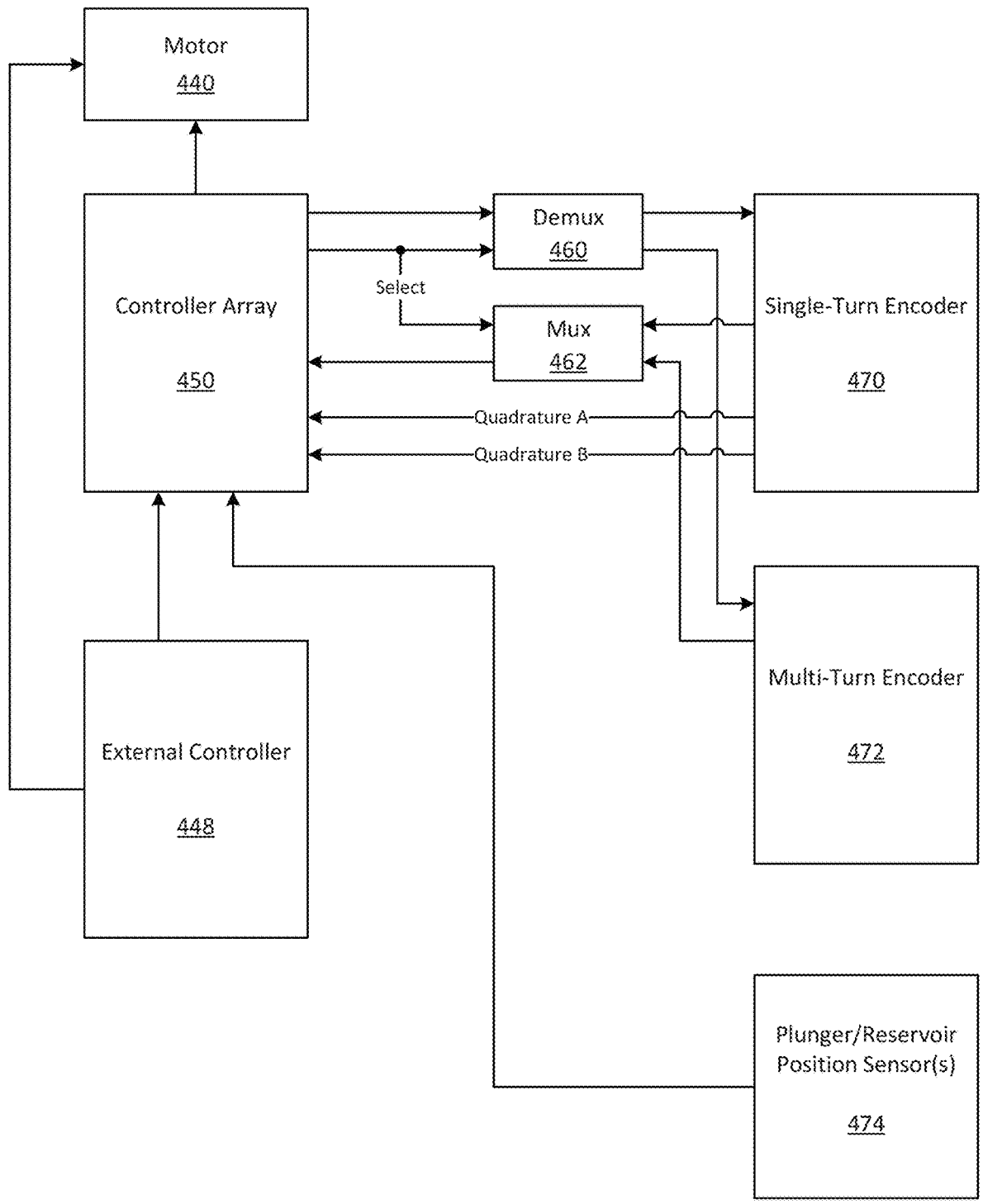
FIG. 4 is a schematic diagram illustrating an exemplary arrangement of position sensing elements in an injection system.

FIG. 4 is a schematic diagram illustrating an exemplary arrangement of position sensing elements in an injection system. In the illustrated examples, a controller array 450 is in communication with a motor 440 such that the controller array 450 can control motion of the motor 440, and likewise any associated system components (e.g., plunger shaft, plunger, etc.). An external controller 448 is in communication with the controller array 450. In some examples, the external controller 448 can be used to program various functions into the controller array 450 or to communicate with one or more system components via the controller array

450. In some embodiments, the external controller 448 can be capable of operating the motor 440 directly while bypassing the controller array 450. In other examples, the external controller 448 can communicate with the motor 440 indirectly via the controller array.

In some examples, the position of the plunger within the reservoir can be indicative of an amount of injectable media present in the reservoir and/or an amount of media that has been expelled from the reservoir. The system of FIG. 4 includes one or more plunger/reservoir position sensor(s) 474. Such position sensor(s) 474 can be configured to provide a signal to the controller array 450 indicative of the position of the plunger (e.g., 320) within the reservoir (e.g., 301). In some embodiments, the positions sensor 474 can be a continuous position sensor that provides an output signal representative of the absolute position of the plunger within the reservoir. In other examples, the position sensor 474 can be configured to output a signal whenever the plunger passes by a predetermined location within the reservoir.

As described, in some embodiments, a system can include one or more rotary encoders positioned on the motor 440 and configured to output a signal indicative of the rotational position of the motor 440. In the illustrative example of FIG. 4, the system includes a single-turn encoder 470 and a multi-turn encoder 472 each in communication with the controller array 450. The single-turn encoder 470 can be configured to output a single-turn encoder value representative of the rotational position of the motor, and the multi-turn encoder 472 can be configured to output a multi-turn encoder value also representative of the rotational position of the motor.

In some embodiments, signals from rotary encoders, such as the single-turn encoder value and the multi-turn encoder value from the single-turn encoder 470 and the multi-turn encoder 472, respectively, are stable and reliable in a variety of operating conditions, such as in magnetic fields. For instance, some systems (e.g., catheter systems) use various fields (e.g., magnetic fields) to move components (e.g., a catheter) during system operations. Such magnetic fields can impact some position sensing devices, such as magnetic encoders. However, rotary encoders, such as single-turn encoder 470 and multi-turn encoder 472 can be used in such environments without the output values from the encoders being corrupted by external fields.

In the illustrated example, the single-turn encoder 470 and multi-turn encoder 472 are in communication with the controller array 450 via a multiplexer 462 and a demultiplexer 460. In some such examples, the controller can selectively send signals to the single-turn encoder 470 and the multi-turn encoder 472 via the demultiplexer 460 and selectively receive signals to the single-turn encoder 470 and the multi-turn encoder 472 via the multiplexer 462. The controller array 450 can output a "Select" signal to the demultiplexer 460 and the multiplexer 462 in order to designate which of the single-turn encoder 470 and the multi-turn encoder 472 is in communication with the controller array 450.

In some embodiments, the controller array 450 can sample a single-turn encoder value output from the single-turn encoder 470 and/or a multi-turn encoder value output from the multi-turn encoder 472, and determine from one or both of the received values a position of the motor 440. In some examples, the controller array 450 can be further configured to compare the single-turn encoder value and the multi-turn encoder value. In some such examples, comparing the single-turn encoder value and the multi-turn encoder vale comprises determining a rotational position of the motor based on the single-turn encoder value and a rotational position of the motor based on the multi-turn encoder vale and comparing the determined rotational positions.

In general, such comparisons of the detected motor position from both the single-turn encoder 470 and the multi-turn encoder 472 can be used as a redundant analysis of the rotational position of the motor. That is, if the detected motor positions agree, then it is likely that the detected position is accurate. However, if the two values are significantly different, then there is likely an error in at least one of the values, which can lead to uncertainty in the position of the motor and similarly, of the plunger shaft and the plunger. Accordingly, in some embodiments, the controller array 450 can be configured to compare the rotational position represented by the single-turn encoder value and the rotational position represented by the multi-turn encoder, and if the difference is greater than a predetermined threshold, disable operation of the motor 440. Disabling operation of the motor 440 can prevent motion of the motor 440 to undesired locations, such as locations that can cause damage to a patient or system equipment.

In the illustrative example of FIG. 4, the single-turn encoder 470 includes quadrature output signals, Quadrature A and Quadrature B. In some such examples, single-turn encoder value comprises at least two such signals in quadrature. The controller array 450 can be configured to receive the quadrature signals from the single-turn encoder, for example, via a quadrature counter. In some embodiments, the controller array 450 utilizes the received quadrature signals to determine various aspects regarding providing operating signals to the motor 440, such as at which angle to energize the motor stator, for example.

In some embodiments, the controller array 450 is programmed with a known correlation between the quadrature counter and the expected position of the plunger within the reservoir. Similarly, the controller array 450 can be configured to determine a position of the plunger based on the single-turn encoder value and/or the multi-turn encoder value. Thus, in some embodiments, the controller array 450 can compare quadrature values from the quadrature counter values stored in the controller array 450 with one or both of the single-turn encoder value and the multi-turn encoder vale. If the difference between the expected position of the plunger based on the quadrature counter is sufficiently different than the expected position of the plunger based on the single-turn encoder value or the multi-turn encoder value, then there is likely an error in one or more values. In some such embodiments, if the difference is greater than a predetermined threshold, the controller array 450 can disable operation of the motor 440 to prevent any unintended operation.

In general, the controller array 450 can be configured to analyze a plurality of signals representative of the position of the plunger within the reservoir. Such signals can include, for example, the single-turn encoder value, the multi-turn encoder value, quadrature/quadrature counter values, a signal from the plunger/reservoir position sensor 474, or the like. In various embodiments, the controller array 450 can be configured to compare two or more such signals to see if the represented plunger location is consistent among the compared signals. If not (e.g., if the difference exceeds a predetermined threshold), the controller array 450 can disable operation of the motor 440. As described, in some examples, comparing the difference in position represented by different signals comprises comparing the difference to a predetermined threshold. In various embodiments, the predetermined threshold comprises a percentage difference, for example, determining if the indicated position values are within 1% of each other, within 5% of each other, within 10% of each other, or the like. Additionally or alternatively, the predetermined threshold can include an absolute difference threshold, for example, determining of the indicated position values are within a predetermined distance of one another, such as within 1 cm, within 5 cm, within 10 cm, or the like.

Similarly, in some embodiments in which the plunger/reservoir position sensor 474 provides an output only when the plunger passes by a predetermined location in the reservoir, the controller array 450 can detect when the position sensor 474 outputs an indication of the plunger being within the predetermined location. The controller array 450 can compare the location represented by one or more other signals (e.g., the single-turn encoder value, the multi-turn encoder value, the quadrature counter, etc.) to the predetermined location. If the difference between the location represented by the one or more other signals and is greater than a predetermined threshold, the controller array 450 can disable operation of the motor 440.

In some embodiments, the predetermined threshold(s) used in comparing position signals can be programmed by a user, for example, via external controller 448. Additionally or alternatively, the controller array 450 can be programmed with a plurality of predetermined thresholds. In various examples, different predetermined thresholds can be assigned to different comparisons. For instance, in some embodiments, the predetermined threshold for comparing the single-turn encoder value to the multi-turn encoder value can be different than the predetermined threshold for comparing the quadrature counter value to one or both of the encoder values. In still further examples, different thresholds can be applied during different phases of system operation. For instance, in some examples, the predetermined threshold for comparing the single-turn encoder value and the multi-turn encoder value resulting in disabling the motor 440 can be different depending on if the system is performing an injection operation when compared to a reservoir fill operation. In various embodiments, such different thresholds (e.g., between different system operations and/or between different value comparisons) can be set via a variety of different ways. For example, in some embodiments, such predetermined thresholds can be programmed during a factory calibration, can be manually set or adjusted by a user, can be automatically updated based on the type of equipment being used with the system, or the like.

In some examples, in addition to or alternatively to disabling operation of the motor 440, the controller array 450 can perform one or more additional tasks in response to detecting a discrepancy between position signals from one or more sources. For instance, in some embodiments, if the controller array 450 compares two or more signals representative of the position of the plunger, and the difference between the position indicated by two or more such signals is not above a predetermined threshold, the controller array 450 will not disable the motor 440. In some such examples, the controller array 450 can operate under the assumption that the position indicated by the two or more signals that are not significantly different (e.g., signals for which the difference between them is less than the predetermined threshold) is correct. Further, in some such examples, the controller array 450 can use the position that is assumed to be correct to calibrate any one or more signals for which the indicated position differs from the assumed position is greater than the predetermined threshold such that the difference falls below the threshold.

In some embodiments, in addition to comparing various values during operation, the controller array 450 can be configured to perform various comparisons upon system startup. For example, when staring up the system, the controller array 450 can determine and compare the plunger positions represented by the single-turn encoder value and the multi-turn encoder value. If the difference between such values is greater than a predetermined threshold, the controller array 450 can prevent the motor 440 from operating.

Additionally or alternatively, the controller array 450 can analyze the value at the quadrature counters for synchronizing any excitation signals to by applied to the motor 440 to the rotor position. In some examples, upon startup, the controller array 450 is configured to initialize the quadrature counter to zero and determine an initial offset value to synchronize any excitation signals to by applied to the motor 440 to the rotor position. Thus, if the motor 440 is enabled (e.g., if the positions indicated by the single-turn encoder value and the multi-turn encoder value are sufficiently similar), the controller array 450 can provide properly calibrated excitation signals to the motor 440 to initiate motor 440 operation.

In some embodiments, one or more operations described with respect to the controller array 450 can be performed by the external controller 448. For example, in some such embodiments, the external controller 448 can receive signals present in the controller array 450 and perform any of a variety of comparisons or other analysis. Similarly, the external controller can enable and/or disable motor 440 operation, for example, via the controller array 450.

In various examples, the controller array 450 can include one or more components configured to operate in conjunction to perform the tasks described herein. For instance, in some embodiments, the controller array 450 can include one or more controllers configured to operate separately or in conjunction with one another. Exemplary controllers can be embodied as one or more microcontrollers. In some embodiments, controllers can include one or more programmable processors programmed with instructions to execute one or more tasks. In some such examples, the controller can include or otherwise be in communication with memory, such as one or more computer-readable media, including instructions for causing the one or more programmable processors for carrying out such functions. Additionally or alternatively, the controller array 450 can include circuitry arranged to perform prescribed tasks, such as an application-specific integrated circuit (ASIC), or the like.

Figure 5:
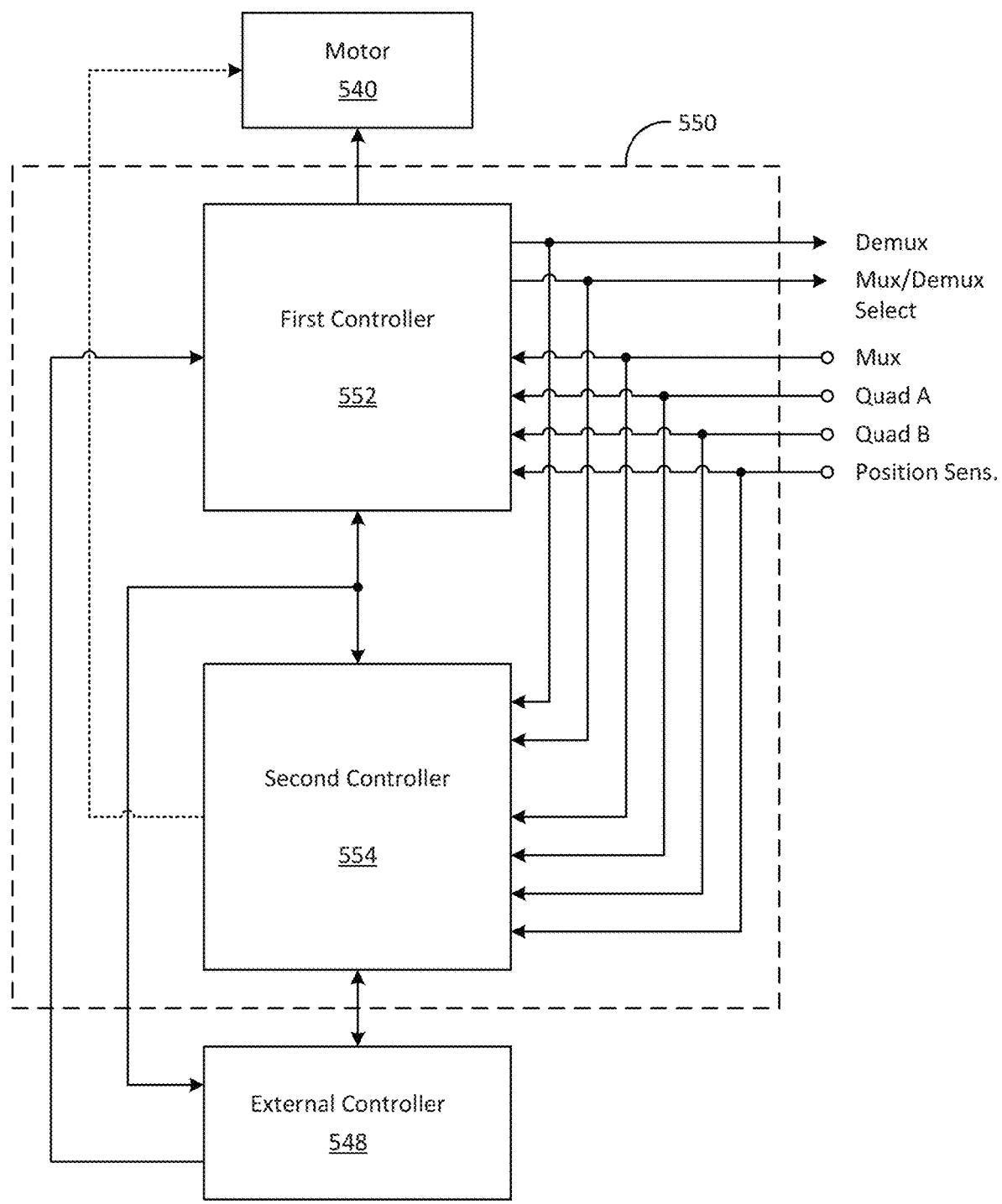
FIG. 5 is a schematic diagram showing a controller array including two separate controllers.

FIG. 5 is a schematic diagram showing a controller array including two separate controllers. In the illustrative example of FIG. 5, the controller array 550 includes a first controller 552 and a second controller 554. As described elsewhere herein, controllers 552 and 554 can include, for example, one or more microcontrollers, programmable processors, ASICs, and/or a variety of other such features.

In some examples, a plurality of controllers (e.g., 552, 554) can be configured in a master/slave relationship. In the illustrated example, first controller 552 is configured to act as a master controller, while second controller 554 functions as a slave controller 554. In some configurations, the first controller 552, the second controller 554, and communication with other system components (e.g., the single-turn encoder and the multi-turn encoder) can be performed using an SPI interface. During exemplary operation, the first controller 552, acting as the master controller, selects a first encoder from one of the single-turn encoder and the multi-turn encoder (e.g., via the Mux/Demux Select signal), and receives data from the selected first encoder via the Mux signal. The second controller 554 similarly receives the signal from the selected first encoder on the Mux signal, as well as the Mux/Demux Select signal to indicate which of the encoders is selected.

In some such embodiments, the first controller 552 subsequently selects the other of the single-turn encoder and the multi-turn encoder as a second encoder via the Mux/Demux Select signal, and receives data from the second encoder via the Mux signal. The second controller 554 similarly receives the signal from the selected second encoder on the Mux signal, as well as the Mux/Demux Select signal to indicate which of the encoders is selected.

After such data collection, both the first controller 552 (acting as the master controller) and the second controller 554 (acting as the slave controller) includes data from each of the single-turn encoder and the multi-turn encoder. In various embodiments, one or both of the first controller 552 and the second controller 554 compares the data received from the multi-turn encoder to the data received from the single-turn encoder. If the difference between the position indicated by the data received from the multi-turn encoder and/or the single-turn encoder is greater than a predetermined threshold, the first controller 552 and/or the second controller 554 can disable operation of the motor 540.

In some embodiments, both the first controller 552 and the second controller 554 are capable of disabling the motor directly. In other examples, the second controller 554 is configured to output to the first controller 552 the results of the data comparison, and the first controller 552 can disable the motor 540 if necessary based on the received comparison data.

In some examples, the first controller 552 (acting as the master controller) repeatedly cycles between collecting data from the single-turn encoder and the multi-turn encoder, for example, via the multiplexer and demultiplexer. The same comparison process can be performed for each data cycle to confirm the position indicated by the single-turn encoder and the multi-turn encoder are consistent with one another. If the position indicated by the single-turn encoder and the multi-turn encoder differ by less than the predetermined threshold amount, operation of the motor/system can continue. The process can be repeated until system use is complete or the controller array 550 disables operation of the motor 540 based on discrepancies in the received encoder data.

In some examples, only one of the controllers (e.g., the first controller 552 and/or the master controller) controls operation of the motor 540, for example, by energizing the motor based on quadrature counter values to initiate motor movement. However, in such embodiments, the other controller (e.g., the second controller 554 and/or the slave controller) can be capable of disabling the motor 540, for example, based on detected unexpected or inconsistent motion and/or position (e.g., via comparison of data from single-turn encoder and multi-turn encoder).

In the illustrated example of FIG. 5, an external controller 548 is in communication with the first controller 552 and the second controller 554. The external controller 548 can include an external workstation, such as control panel 102 of FIG. 1, or a user's personal device, such as a computer, smartphone, tablet, or the like. The external controller 548 can communicate with one or both of the first controller 552 and the second controller 554 via a wired or wireless communication.

In some examples, the external controller 548 receives data from the first controller 552 and/or the second controller 554 representative of the data received from the single-turn encoder and/or the multi-turn encoder. The external controller 548 can be configured to analyze the received data, such as via comparing a position indicated by the signals provided by the single-turn encoder and the multi-turn encoder. In some cases, if the difference in such indicated positions in greater than a predetermined threshold, the external controller 548 can disable operation of the motor 540, either directly or via the first controller 552 and/or the second controller 554.

Additionally or alternatively, the external controller 548 can be used to program the first controller 552 and/or the second controller 554, for example, by defining predetermined threshold used for comparing position information. In some examples, external controller 548 can be used to execute one or more predetermined injection system operations (e.g., a reservoir fill process, an injection process, etc.) by controlling the motor 540 via the first controller 552 and/or the second controller 554.

Figure 6:
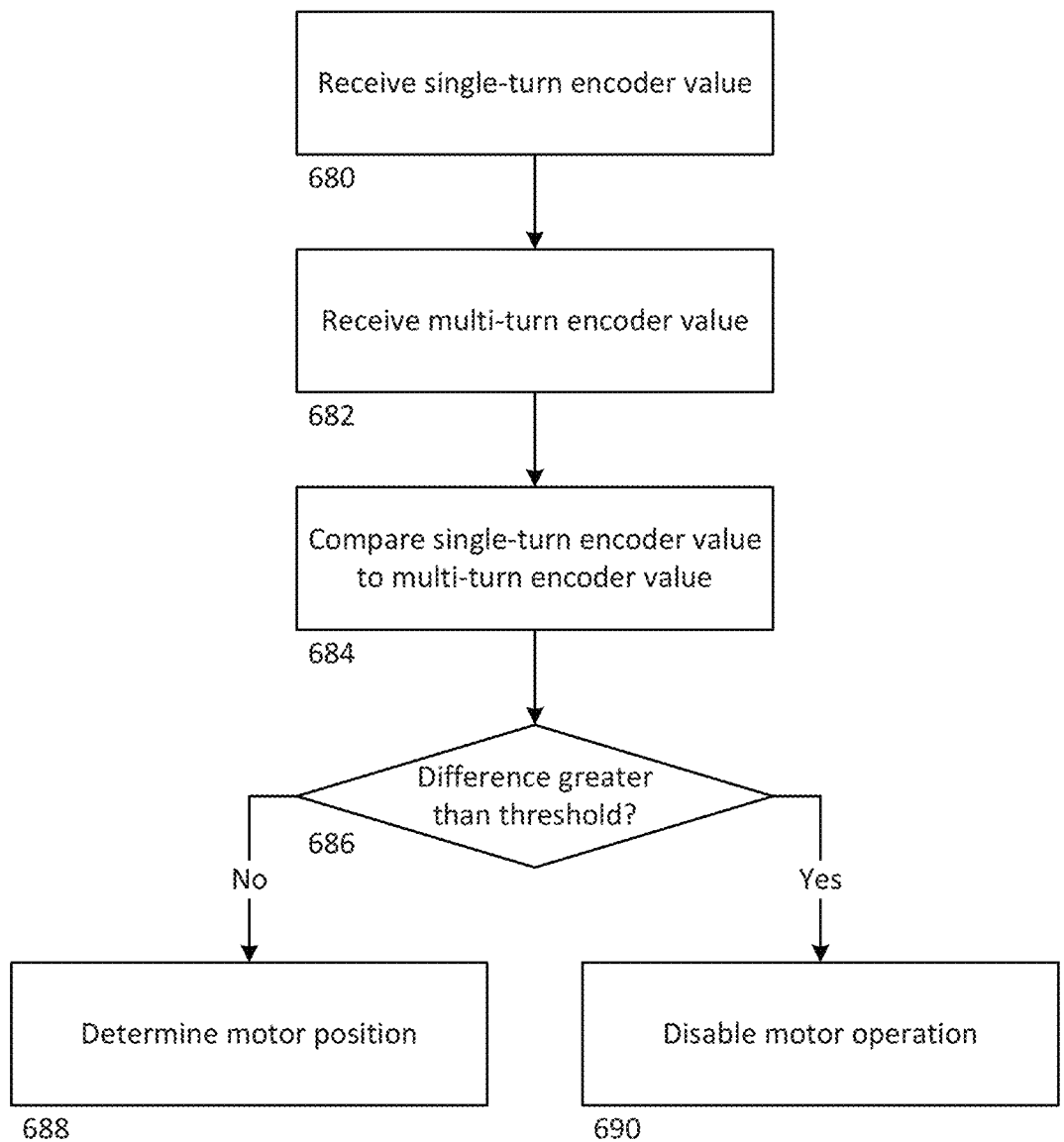
FIG. 6 is a process flow diagram showing an exemplary process for determining a motor position in an injection system.

FIG. 6 is a process flow diagram showing an exemplary process for determining a motor position in an injection system. The method shown in FIG. 6 includes receiving a single-turn encoder value (680), for example, from single-turn encoder 470, and receiving a multi-turn encoder vale (682), for example, from multi-turn encoder 472. The method further includes comparing the single-turn encoder value to the multi-turn encoder value (684), and determining if the difference between the values is greater than a predetermined threshold (686). In some examples, comparing the single-turn encoder value to the multi-turn encoder value (684) can comprise directly comparing the received raw values. In other examples, comparing the single-turn encoder value to the multi-turn encoder value (684) can include determining a common metric (e.g., a motor and/or plunger position) associated with each of the received values and comparing the common metric.

If the difference is not greater than the predetermined threshold, then the motor position can be determined (688), for example, based on the single-turn encoder value and/or the multi-turn encoder value. In some examples, additional or alternative data can be similarly determined, such as a plunger position within a reservoir, a volume of injectable media in the reservoir, a volume of injectable media that has been injected, and the like. However, in the event that the difference is greater than the predetermined threshold, motor operation can be disabled (690). As described elsewhere herein, the motor can be disabled via a controller array (e.g., 550 in FIG. 5), such as via a master controller or a slave controller, and/or via an external controller (e.g., 548 in FIG. 5).

Figure 7:
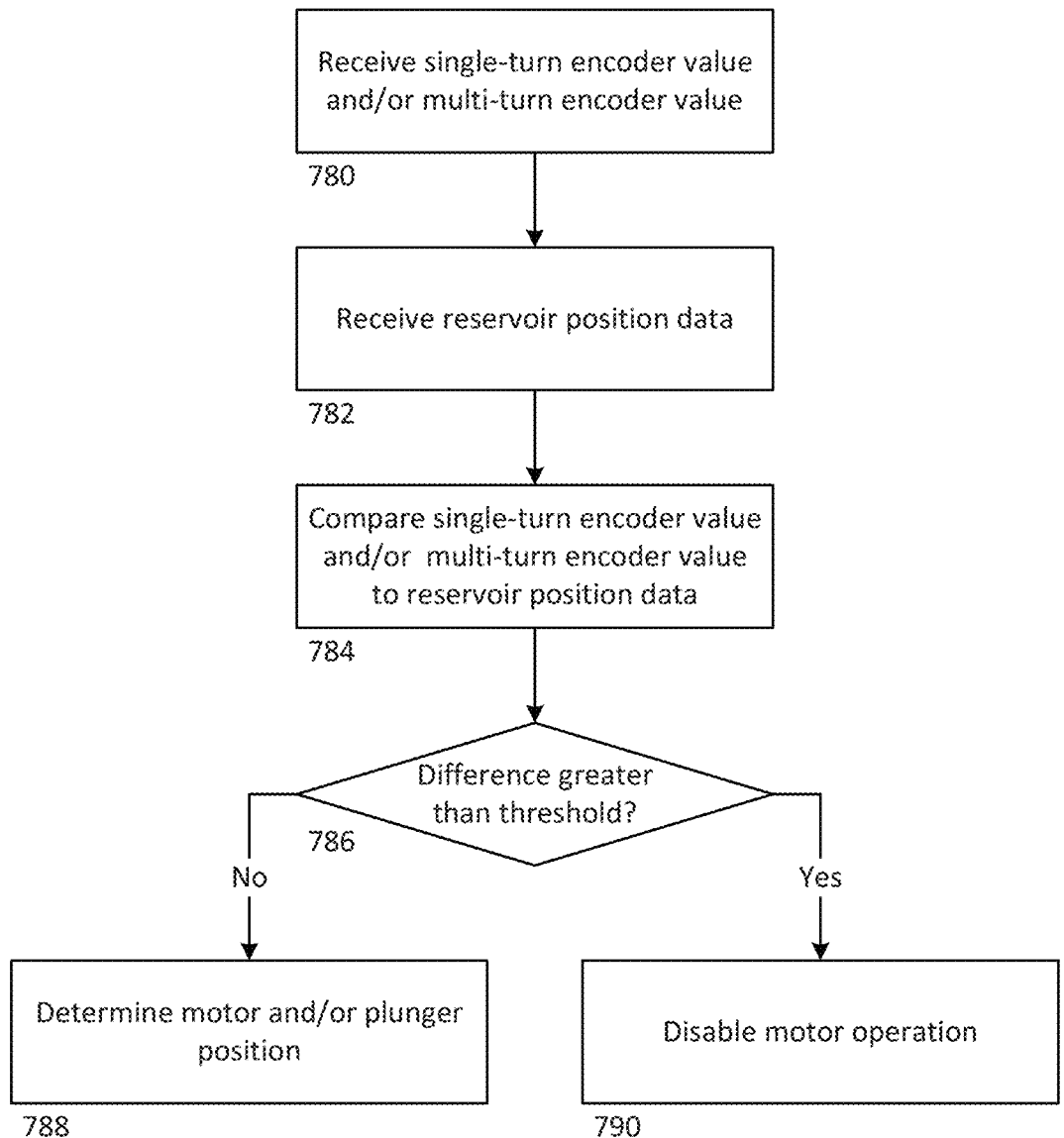
FIG. 7 is a process flow diagram showing another exemplary process for determining a motor position in an injection system.

FIG. 7 is a process flow diagram showing another exemplary process for determining a motor position in an injection system. The method shown in FIG. 7 includes receiving a single-turn encoder value and/or a multi-turn encoder (780), for example, from single-turn encoder 470 and/or multi-turn encoder 472 in FIG. 4, and receiving reservoir position data, for example, from position sensor 474 in FIG. 4. The method further includes comparing the single-turn encoder value and/or the multi-turn encoder vale to the received reservoir position data (784), and determining if the difference between the values is greater than a predetermined threshold (786). In some examples, comparing the single-turn encoder value and/or the multi-turn encoder value to the reservoir position data (784) can comprise directly comparing the received raw values (e.g., raw data received from single-turn encoder 470 and/or multi-turn encoder 472 with raw data from position sensor 474). In other examples, comparing the single-turn encoder value and/or the multi-turn encoder value to the reservoir position data (784) can include determining a common metric (e.g., a motor and/or plunger position) associated with each of the received values and comparing the common metric.

If the difference is not greater than the predetermined threshold, then the position of the motor and/or the plunger can be determined (788), for example, based on the single-turn encoder value, the multi-turn encoder value, and/or the reservoir position data. In some examples, additional or alternative data can be similarly determined, such as a plunger position within a reservoir, a volume of injectable media in the reservoir, a volume of injectable media that has been injected, and the like. However, in the event that the difference is greater than the predetermined threshold, motor operation can be disabled (790). As described elsewhere herein, the motor can be disabled via a controller array (e.g., 550 in FIG. 5), such as via a master controller or a slave controller, and/or via an external controller (e.g., 548 in FIG. 5).

Figure 8:
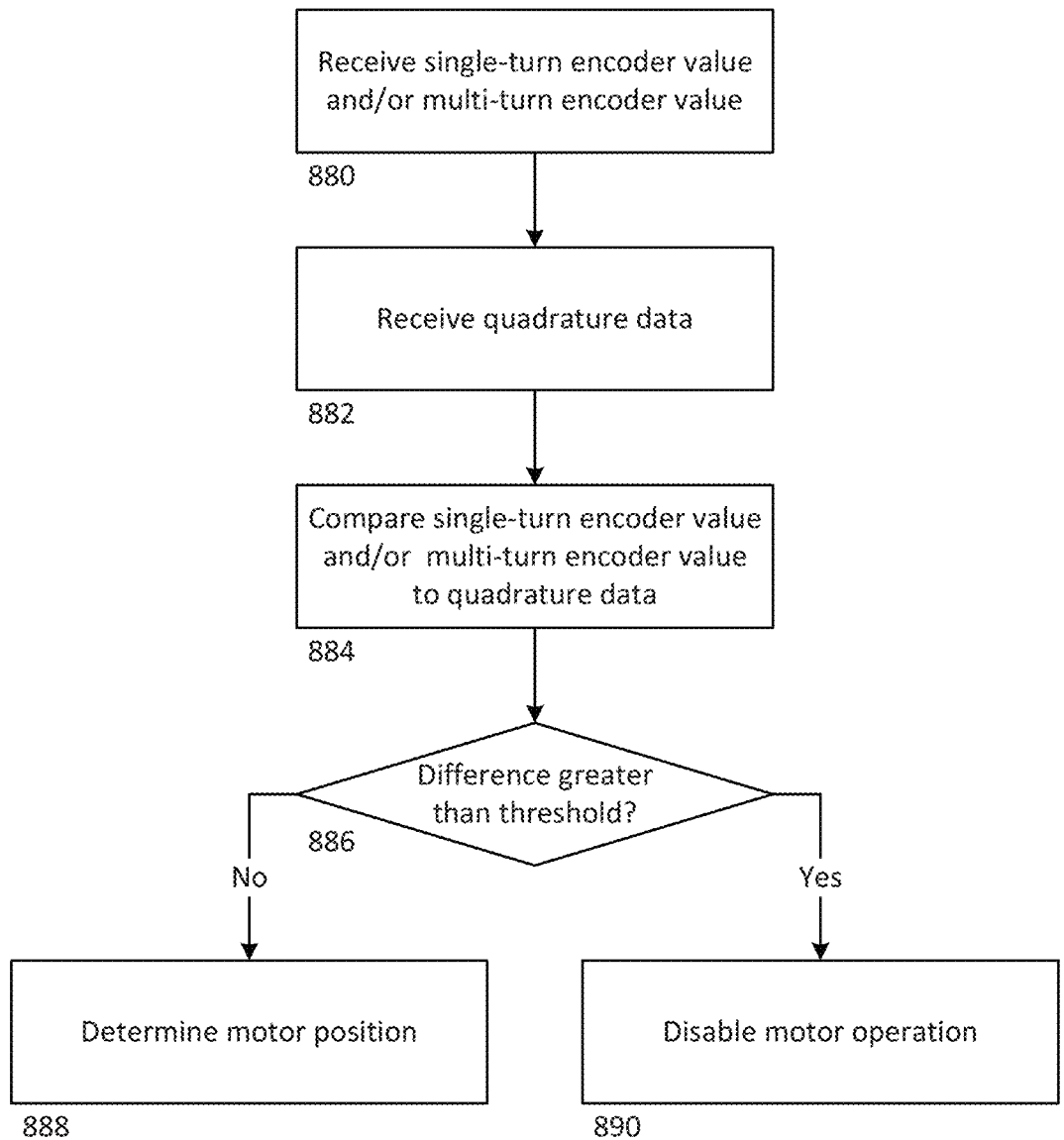
FIG. 8 is a process flow diagram showing another exemplary process for determining a motor position in an injection system.

FIG. 8 is a process flow diagram showing another exemplary process for determining a motor position in an injection system. The method shown in FIG. 8 includes receiving a single-turn encoder value and/or a multi-turn encoder (880), for example, from single-turn encoder 470 and/or multi-turn encoder 472 in FIG. 4, and receiving quadrature data, such as a quadrature counter value, for example, from a quadrature counter in a controller array. The method further includes comparing the single-turn encoder value and/or the multi-turn encoder vale to the received quadrature data (884), and determining if the difference between the values is greater than a predetermined threshold (886). In some examples, comparing the single-turn encoder value and/or the multi-turn encoder value to the quadrature data (884) can comprise directly comparing the received raw values (e.g., raw data received from single-turn encoder 470 and/or multi-turn encoder 472 with raw quadrature data from a quadrature counter). In other examples, comparing the single-turn encoder value and/or the multi-turn encoder value to the quadrature data (884) can include determining a common metric (e.g., a motor and/or plunger position) associated with each of the received values and comparing the common metric.

If the difference is not greater than the predetermined threshold, then the position of the motor and/or the plunger can be determined (888), for example, based on the single-turn encoder value, the multi-turn encoder value, and/or the quadrature data. In some examples, additional or alternative data can be similarly determined, such as a plunger position within a reservoir, a volume of injectable media in the reservoir, a volume of injectable media that has been injected, and the like. However, in the event that the difference is greater than the predetermined threshold, motor operation can be disabled (890). As described elsewhere herein, the motor can be disabled via a controller array (e.g., 550 in FIG. 5), such as via a master controller or a slave controller, and/or via an external controller (e.g., 548 in FIG. 5).

Figure 9:
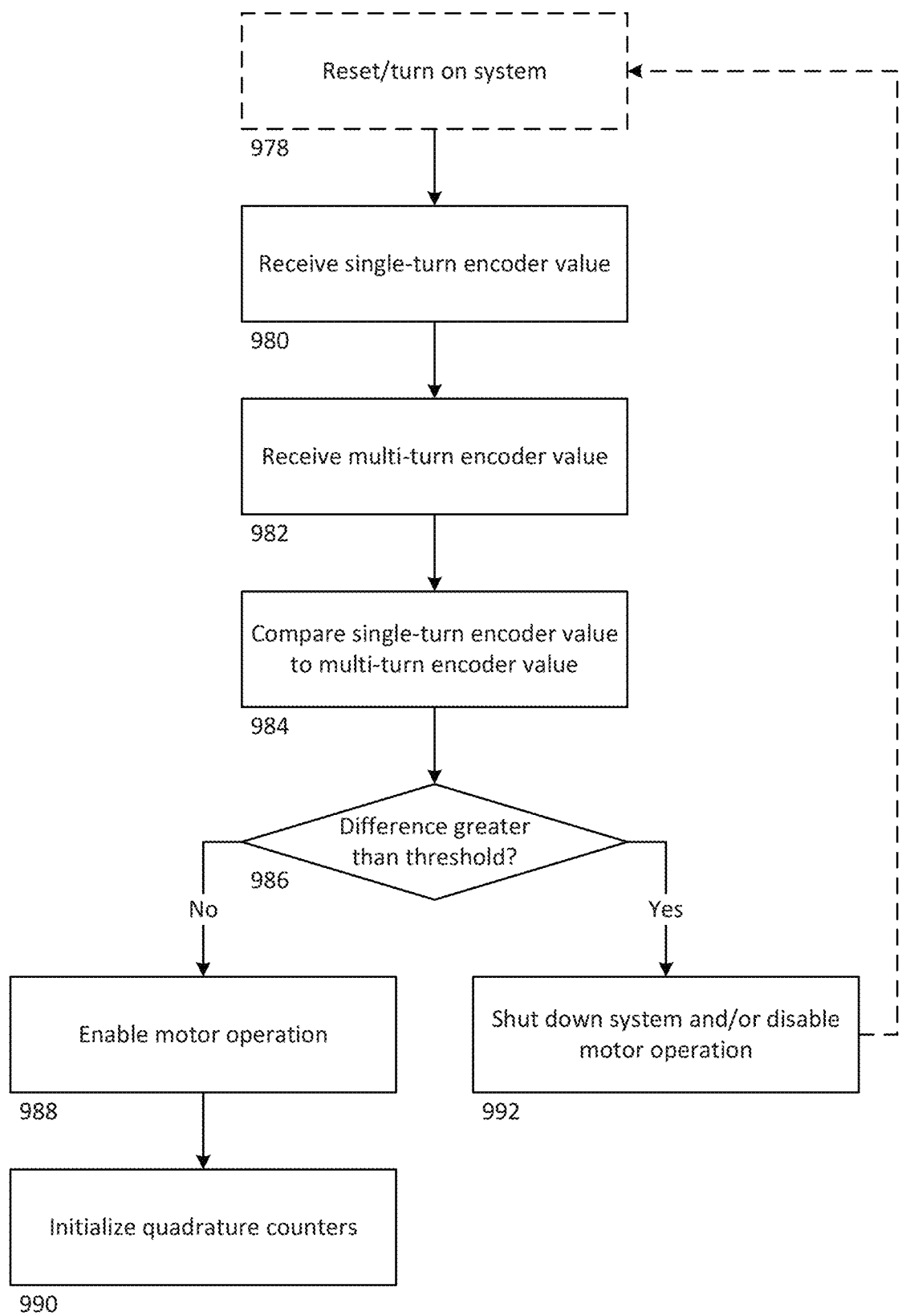
FIG. 9 is a process flow diagram showing an exemplary process for enabling motor operation, for example, after the motor has been disabled or the system has been shut down.

FIG. 9 is a process flow diagram showing an exemplary process for enabling motor operation, for example, after the motor has been disabled or the system has been shut down. The method shown in FIG. 9 includes receiving a single-turn encoder value (980), for example, from single-turn encoder 470, and receiving a multi-turn encoder vale (982), for example, from multi-turn encoder 472. The method further includes comparing the single-turn encoder value to the multi-turn encoder value (984), and determining if the difference between the values is greater than a predetermined threshold (986). In some examples, comparing the single-turn encoder value to the multi-turn encoder value (984) can comprise directly comparing the received raw values. In other examples, comparing the single-turn encoder value to the multi-turn encoder value (984) can include determining a common metric (e.g., a motor and/or plunger position) associated with each of the received values and comparing the common metric.

If the difference is not greater than the predetermined threshold, then motor operation can be enabled (988), for example, after a system startup process or after the motor had been previously disabled (e.g., per a method shown in any of FIGS. 6-8). In some examples, in addition to enabling motor operation (988), the method can include initializing quadrature counters (990), for example, in the controller array 450. Initializing quadrature counters can ensure that the drive signals provided by the controller array (e.g., 450) to the motor (e.g., 440) are properly coordinated.

However, in the event that the difference between the single-turn encoder value and the multi-turn encoder value is greater than the predetermined threshold, the system can be shut down and/or the motor operation can be disabled (992). As described elsewhere herein, shutting down the system and/or disabling the motor can be performed via a controller array (e.g., 550 in FIG. 5), such as via a master controller or a slave controller, and/or via an external controller (e.g., 548 in FIG. 5). In some examples, after the system is shut down and/or the motor is disabled (992), the system can be reset or turned on (978) to perform system operation. In some such examples, the process repeats, as shown in FIG. 9, and motor operation is not enabled (988) until the difference between the single-turn encoder value and the multi-turn encoder values is not greater than the threshold (986).

Various methods described with respect to FIGS. 6-9 include comparing values to various predetermined thresholds. However, it will be appreciated that such thresholds need not be same between various methods. For example, the predetermined threshold used to compare the single-turn encoder value and the multi-turn encoder value in the method of FIG. 6 can be different from the predetermined threshold used to compare the single-turn encoder value and/or multi-turn encoder value and the quadrature data in FIG. 8.

Similarly, different thresholds can be used when comparing data for different processes. For example, in some embodiments, the threshold above which the difference between the single-turn encoder value and the multi-turn encoder value to cause the motor operation to be disabled according to FIG. 6 can be different from the threshold value below which the motor operation is enabled according to FIG. 9. For instance, in some examples, the threshold above which the difference between the single-turn encoder value and the multi-turn encoder value to cause the motor operation to be disabled can (e.g., according to FIG. 6) be greater than the threshold value below which the motor operation is enabled (e.g., according to FIG. 9). In other examples, the threshold above which the difference between the single-turn encoder value and the multi-turn encoder value to cause the motor operation to be disabled (e.g., according to FIG. 6) can be lower than the threshold value below which the motor operation is enabled (e.g., according to FIG. 9).

Such various comparisons and thresholds as described with respect to FIGS. 6-9 provide various levels of redundancy in determining and/or monitoring the position(s) of one or more components in an injector system. Having multiple data streams representing, for example, the position of a plunger within a reservoir can provide redundancy by confirming a first data stream is likely to indicate a correct plunger position. As described elsewhere herein, accurate position monitoring of the plunger can be used for various processes, such as properly filling the reservoir, injecting a predetermined amount from the reservoir, preventing undesired reuse of the reservoir, and the like. Errors in position sensing can lead to errors in such processes, which can risk the safety of the patient and/or the equipment. Providing one or more redundant data streams representing the position of the plunger can help reduce such errors and increase safety of the system.

Various examples have been described. However, it will be appreciated that various modifications and changes can be made without departing from the scope of the invention as set forth in the appended claims.

What is claimed is:

1. An injection system comprising:
   a reservoir including an inner surface;
   a plunger mounted within the reservoir and including an outer surface configured to engage with the inner surface of the reservoir;
   a plunger shaft including a terminal portion configured to engage the plunger within the reservoir;
   a motor coupled to the plunger shaft and configured to cause the plunger shaft and plunger to move linearly within the reservoir when the motor is actuated;
   a multi-turn encoder in communication with the motor and configured to output a multi-turn encoder value representative of a rotational position of the motor;
   a single-turn encoder in communication with the motor and configured to output a single-turn encoder value representative of a rotational position of the motor; and
   a controller array configured to:
   receive the multi-turn encoder value from the multi-turn encoder;
   receive the single-turn encoder value from the single-turn encoder; and
   determine a position of the plunger within the reservoir based on at least one of the multi-turn encoder value and the single-turn encoder value.

2. The injection system of claim 1, wherein the controller array is further configured to:
   compare the rotational position represented by the multi-turn encoder value and the rotational position represented by the single-turn encoder value; and
   if the difference between the compared rotational positions is greater than a predetermined amount, disable the motor.

3. The injection system of claim 1, wherein the single-turn encoder value from the single-turn encoder comprises two signals in quadrature.

4. The injection system of claim 3, wherein the controller array comprises a quadrature counter and is configured to control operation of the motor based on a quadrature counter value.

5. The injection system of claim 4, wherein the controller array is further configured to:
   compare the quadrature counter value to the multi-turn encoder value and/or the single-turn encoder value; and
   if the difference between the quadrature counter value and the multi-turn encoder value and/or the difference between the quadrature counter value and the single-turn encoder value is greater than a predetermined value, disable operation of the motor.

6. The injection system of claim 4, wherein, upon startup of the system, the controller array is configured to compare the multi-turn encoder value and the single-turn encoder value, and if the difference between the multi-turn encoder value and the single-turn encoder value is below a predetermined value, enable operation of the motor.

7. The injection system of claim 1, wherein the controller array comprises a first controller and a second controller.

8. The injection system of claim 7, wherein:
   the first controller is configured to:
   receive a first multi-turn encoder value from the multi-turn encoder;
   receive a first single-turn encoder value from the single-turn encoder; and
   compare the first multi-turn encoder value to the first single-turn encoder value to determine a first comparison value;
   the second controller is configured to:
   receive a second multi-turn encoder value from the multi-turn encoder;
   receive a second single-turn encoder value from the single-turn encoder; and
   compare the second multi-turn encoder value to the second single-turn encoder value to determine a second comparison value; and
   wherein the first controller or the second controller is further configured to disable the motor if:
   (i) the first comparison value is greater than a predetermined threshold;
   (ii) the second comparison value is greater than a predetermined threshold;
   and/or (iii) the difference between the first comparison value and the second comparison value is greater than a predetermined threshold.

9. The injection system of claim 1, further comprising a reservoir position sensor in communication with the controller array, and wherein the controller array is configured to:
   receive reservoir position data from the reservoir position sensor;
   compare the received reservoir position data to the determined position of the plunger based on at least one of the multi-turn encoder value and the single-turn encoder value; and
   if the difference between the received reservoir position data and the determined position of the plunger is greater than a predetermined amount, disable operation of the motor.

10. The injection system of claim 1, wherein the multi-turn encoder and the single-turn encoder are mounted to the motor.

11. The injection system of claim 1, wherein, upon startup of the system, the controller array is configured to detect a position of the plunger within the reservoir.

12. The injection system of claim 11, wherein the controller array is configured to
    (i) save determined position information representative of the position of the plunger within the reservoir in memory upon disabling and/or shutting down the system such that the detecting the position of the plunger within the reservoir upon startup comprises recalling the saved position information; and/or
    (ii) receive an initial multi-turn encoder value from the multi-turn encoder and/or an initial single-turn encoder value from the single-turn encoder upon enabling or starting up the system; such that the detecting the position of the plunger within the reservoir upon startup comprises determining an initial position of the plunger based on the received initial multi-turn encoder value and/or the initial single-turn encoder value.

13. The injection system of claim 1, wherein the controller array is further configured to cause the motor to move the plunger shaft such that the plunger moves to a predetermined location within the reservoir based on feedback from the determined position of the plunger within the reservoir.

14. The injection system of claim 13, further comprising a host computer in communication with the controller array, and wherein the controller array is configured to cause the motor to move the plunger shaft such that the plunger moves to the predetermined location within the reservoir in response to a command signal received from the host computer.

15. A method of operating an injection system comprising:
- receiving a multi-turn encoder signal representative of a rotational position of a motor, the motor being configured to impart linear motion of a plunger shaft and a corresponding plunger within a reservoir in the injection system;
- receiving a single-turn encoder signal representative of an absolute rotational position of the motor;
- determining a position of the plunger within the reservoir of the injection system based on one of the received multi-turn encoder signal and the received single-turn encoder signal; and
- confirming the determined position of the plunger within the reservoir based on the other of the received multi-turn encoder signal and the received single-turn encoder signal.

16. The method of claim 15, wherein confirming the determined position of the plunger within the reservoir based on the other of the received multi-turn encoder signal and the single-turn encoder signal comprises comparing the received single-turn encoder signal to the received multi-turn encoder signal.

17. The method of claim 16, further comprising, if the difference between the single-turn encoder signal and the multi-turn encoder signal is greater than a predetermined amount, disabling operation of the motor.

18. The method of claim 15, wherein the single-turn encoder signal comprises a first signal and a second signal in quadrature, and wherein the method further comprises providing an electrical signal to the motor to control operation of the motor, the electrical signal having at least one parameter that is based on the received first and second signals.

19. An injection system comprising:
- a plunger within a reservoir;
- a plunger shaft configured to operatively engage the plunger;
- a motor configured to move the plunger shaft longitudinally with respect to the reservoir such that, when the motor is actuated and when the plunger shaft engages the plunger, the plunger is moved longitudinally within the reservoir;
- a first encoder coupled to the motor and configured to provide a first output representative of a position of the motor;
- a second encoder coupled to the motor and configured to provide a second output representative of the position of the motor;
- a controller array in communication with the motor, the first encoder, and the second encoder, the controller array being configured to:
  receive the first output from the first encoder;
  receive the second output from the second encoder;
  compare the first output to the second output; and
  if the difference between the first output and the second output is greater than a predetermined amount, disable operation of the motor.

20. The injection system of claim 19, wherein the controller array is further configured to:
- determine an absolute position of the plunger within the reservoir based on the first output, the second output, or a combination of the first output and the second output; and
- repeatedly receive updated first and second outputs from the first and second encoders, respectively, and update the determined absolute position of the plunger within the reservoir based on the updated first output, the updated second output, or a combination of the updated first output and the updated second output.

* * * * *